US012676226B2

(12) United States Patent
Bradley et al.

(10) Patent No.: US 12,676,226 B2
(45) Date of Patent: Jul. 7, 2026

(54) PERSONALIZED HEALTH AND FITNESS RECOMMENDATION PLATFORM, SYSTEM AND METHOD

(71) Applicant: Fit Wind LLC, Los Angeles, CA (US)

(72) Inventors: Anne Bradley, Santa Monica, CA (US); Paul Winsper, Lake Oswego, OR (US); Michael Watts, Lake Oswego, OR (US)

(73) Assignee: Fit Wind LLC, Salt Lake City, UT (US)

( * ) Notice: Subject to any disclaimer, the term of this patent is extended or adjusted under 35 U.S.C. 154(b) by 0 days.

(21) Appl. No.: 18/667,867

(22) Filed: May 17, 2024

(65) Prior Publication Data

US 2024/0387017 A1     Nov. 21, 2024

Related U.S. Application Data

(60) Provisional application No. 63/502,659, filed on May 17, 2023.

(51) Int. Cl.
*G16H 20/30*     (2018.01)
*G16H 50/20*     (2018.01)

(52) U.S. Cl.
CPC ............. *G16H 20/30* (2018.01); *G16H 50/20* (2018.01)

(58) Field of Classification Search
CPC ......... G16H 20/30; G16H 50/20; G16H 15/00

USPC ......................................................... 705/2–3
See application file for complete search history.

(56) References Cited

U.S. PATENT DOCUMENTS

| | | | |
|---|---|---|---|
| 2012/0059664 A1* | 3/2012 | Georgiev ............. | A61B 5/1072 705/2 |
| 2021/0001180 A1* | 1/2021 | Wang ..................... | G16H 20/30 |
| 2021/0219874 A1* | 7/2021 | Coyle ................... | G16H 20/30 |
| 2022/0176202 A1* | 6/2022 | Kunitz ............... | A63B 71/0622 |

OTHER PUBLICATIONS

Chatterjee et al., Machine learning and ontology in eCoaching for personalized activity level monitoring and recommendation generation. Sci Rep 12, 19825 (Nov. 18, 2022). https://doi.org/10.1038/s41598-022-24118-4 (Year: 2022).*
Hannan et al., A Portable Smart Fitness Suite for Real-Time Exercise Monitoring and Posture Correction. Sensors. Oct. 8, 2021; 21(19):6692. https://doi.org/10.3390/s21196692 (Year: 2021).*

* cited by examiner

*Primary Examiner* — Joy Chng
(74) *Attorney, Agent, or Firm* — Finn IP Law, PC; Jeffrey A. Finn

(57)     ABSTRACT

The present invention offers a novel, integrated, multi-source input, data-based personalized health, exercise and fitness system and method. The system offers personalized fitness plans based on a user's disparate input sources. The system can ingest both asynchronous and synchronous inputs to improve health fitness results. A screen with camera, preferably in a mirror design is a central component of the invention.

6 Claims, 14 Drawing Sheets

Data Collection

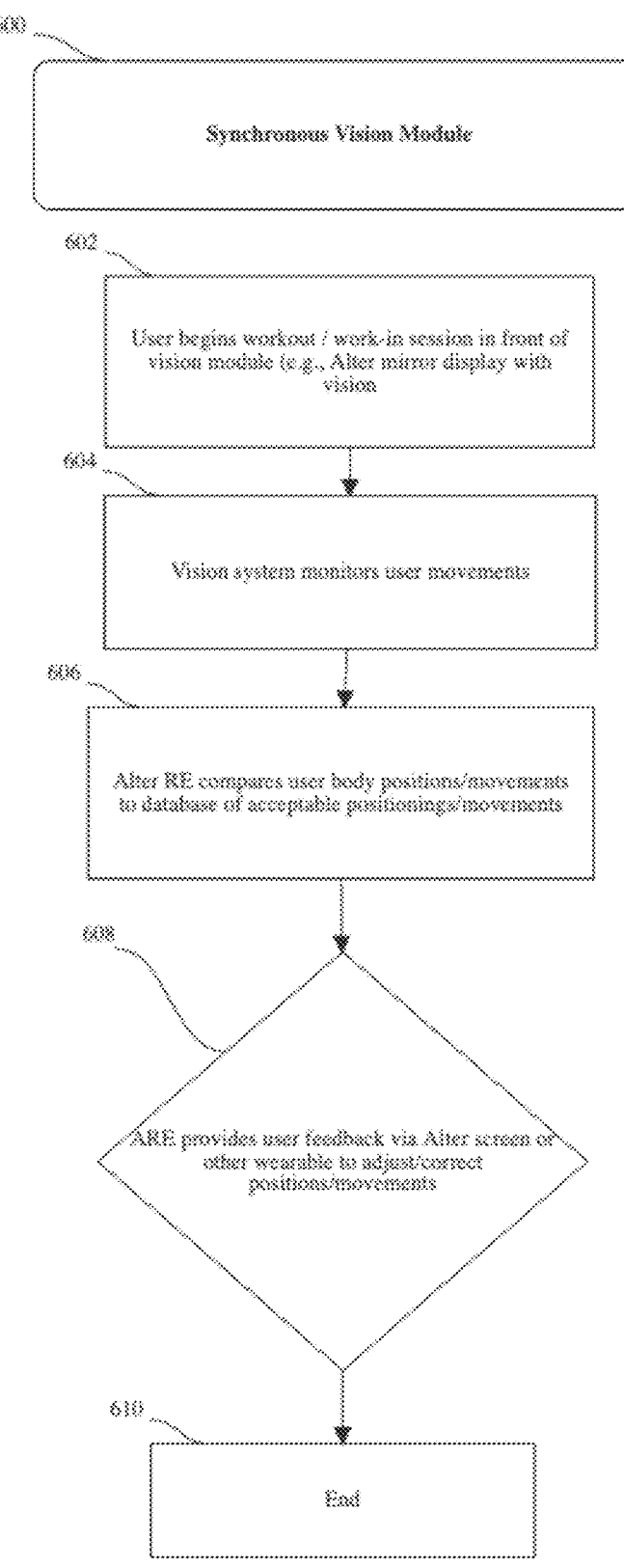

600

Synchronous Vision Module

602

User begins workout / work-in session in front of
vision module (e.g., Alter mirror display with
vision

604

Vision system monitors user movements

606

Alter RE compares user body positions/movements
to database of acceptable positionings/movements

608

ARE provides user feedback via Alter screen or
other wearable to adjust/correct
positions/movements

610

End

FIG. 6

PERSONALIZED HEALTH AND FITNESS RECOMMENDATION PLATFORM, SYSTEM AND METHOD

REFERENCE TO RELATED APPLICATIONS

This application claims the benefit of U.S. Provisional Application No. 63/502,659, filed May 17, 2023, the contents of each of which are incorporated by this reference in their entirety for all purposes as if fully set forth herein.

BACKGROUND OF THE INVENTION

The present invention pertains to the field of personalized health, fitness and wellness platforms for individuals.

Achieving and maintaining physical fitness and mental wellness for all age groups through cardiovascular (aerobic) exercise, resistance training, and through proper rest, breathing and mindfulness techniques, such as yoga and meditation, to name a few, are important and interrelated factors in maintaining good health and mental balance, and in preventing various injuries and chronic diseases. As used hereinafter, physical exercise routines will be called "workouts", and conventionally less physical exercises, including mindful yoga, breathing and stretching routines will be called "work-in's". All such activities will generally be referred to as "fitness" routines. However, fitness recommendations for the general population are typically generic to broad segments of that population (e.g., by age groups or self-reported fitness status). They are not conventionally tailored to an individual's specific wants, needs, risk factors and goals. Furthermore, unless they have personal trainers, it can be challenging for individuals to track their own fitness progress, make corrections during their exercise routines and adjust their sets of routines (intensity, quantity, such as reps and mix of exercises) whether because of improvement to their fitness or because of setbacks.

In recent years, many technologies have been developed to monitor discrete aspects of an individual's state of health and fitness and provide data metrics for these aspects. As used herein, "asynchronous monitoring" refers to personal inputs relating to an individual's state of health and exercise readiness that are collected at a time prior to a workout or work-in-"a fitness event"-such as one-time genetic testing and analysis and nightly sleep tracking. "Synchronous monitoring" on the other hand, refers herein to personal data inputs that are collected and used for individual feedback in real time or near real time. Examples of synchronous monitoring include smart watches and related exercise apps that can monitor instantaneous heart rate and visual sensing and monitoring of an exerciser's positions while exercising. Some monitoring can be simultaneously synchronous and asynchronous, such as V02 monitoring that measures an exerciser's cardio capacity during aerobic exercise, like running. For example, an instantaneous VO2 reading can be used during a run to tell the runner to push harder or run slower. It can also be in an asynchronous data point in the development of a personalized running routine.

Either of these categories of personal data inputs gathered from these technologies alone can provide valuable insights into an individual's physical needs and capabilities. Sometimes they may even be combined by, say, a physical trainer, to provide some measure of personalized exercise recommendations. Unfortunately, no fitness devices or systems are truly fully automated and comprehensive for providing a person a customized and constantly evolving fitness plan unique to each person. What's needed is a technologically advanced, integrated and flexible platform for any individual that can collect multiple streams of both asynchronous and synchronous monitored personal outputs from disparate sources to create a truly integrated, recommendation engine that automatically personalizes, customizes and on the fly adjusts, a fitness plan for the individual both in real time and for the long-term health and wellness of the individual.

SUMMARY OF THE INVENTION

The present invention meets these needs and more by disclosing a truly integrated personalized exercise recommendation engine that receives user data inputs from numerous disparate sources to collect a user's self-reporting, genetic profile, sleep profile, and visual sensing to provide tailored and always adjusting fitness plans and recommendations to individual users. The exercise recommendation engine may implement machine learning algorithms to analyze the asynchronous and synchronous inputs to generate individualized workouts and work-ins, live coaching inputs to improve exercise form, and other recommendations that are specific to the individual's goals, physical capabilities, and preferences.

The present invention discloses a multi-source input fitness and health recommendation engine for a user. The engine includes a data collection module that collects user data from multiple input sources. It also includes a data processing module that processes the data and applies algorithms including in embodiments machine learning algorithms to create and improve upon a personalized exercise plan for the user. The engine also includes a recommendation generation module that provides the user with recommended exercises. In embodiments, the multiple input sources comprise synchronous data inputs and asynchronous data inputs. Asynchronous data inputs may include, for example, data gathered from one or more of a self-reporting module, a captured DNA report module, and a sleep tracking module. Synchronous data inputs may include data selected from one or more of from visually captured user movement, heart rate, heart rate variability, and self-reporting during a workout. These are just a few exemplary combinations of inputs enabled by the present invention.

In embodiments, the recommended exercises comprise a plan for workouts and work-ins, include at least exercise types, a number of reps per exercise type, sets, and rest periods between sets. The exercises may be provided to the user via pre-recorded videos selected from a library of videos. Or the recommended exercises may be provided to the user via live instruction provided on a screen.

In some embodiments, the recommendation engine can create and export a customized exercise and fitness report for the user. This may be sent to the user via conventional methods such as email, phone or to a dedicated user app, to name a few.

The present invention also discloses methods of and systems for creating a customized fitness and health plan for a user, using the inputs and recommendation engine as described in any of the above options.

BRIEF DESCRIPTION OF THE FIGURES

Further advantages of the present invention may become apparent to those skilled in the art with the benefit of the following detailed description of the preferred embodiments and upon reference to the accompanying drawings in which:

FIG. 6 is a simplified flow diagram showing the operation of a synchronous vision input module according to one embodiment of the present invention;

DETAILED DESCRIPTION OF THE INVENTION

Figure 1:
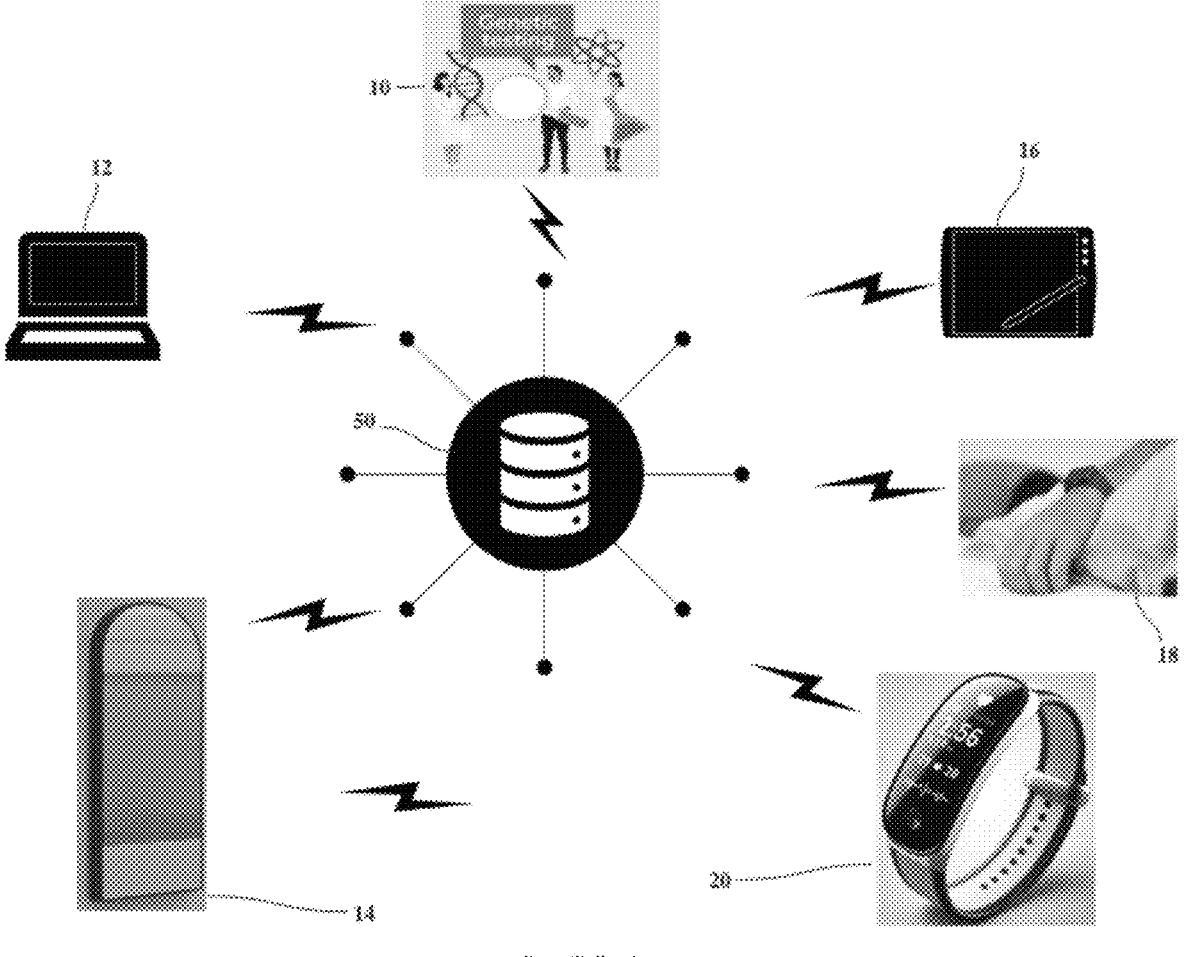
FIG. 1 is an illustrative block diagram showing personalized data capturing systems that may provide inputs to the recommendation engine of the present invention.

The automated personalized fitness platform of the present invention comprises multiple personalized data input modules that are input into a specialized recommendation engine to provide customized fitness plans and real-time feedbacks for users of the platform. In basic embodiments, the platform comprises a DNA input module, a sleep metrics module, a heart (and potentially other metrics) monitoring module, visual sensing module, and a recommendation engine that may include machine learning algorithms. The DNA input module analyzes the individual's DNA to identify genetic factors that can impact their physical performance and fitness. The sleep metrics module tracks the individual's sleep patterns and quality to determine the optimal time for exercise and rest. The visual sensing module uses cameras and sensors to analyze the individual's movements and posture during exercise, providing real-time feedback and monitoring.

The RE algorithm combines the data from the DNA input module, sleep metrics module, and visual sensing module to generate personalized exercise recommendations. The algorithm may take into account the individual's physical capabilities, preferences, and goals, as well as external factors such as weather conditions and location. The recommendations can be delivered through a user interface, such as a mobile app or website, and can be updated and adjusted based on the individual's progress and feedback.

Referring now to the drawings, like reference numerals designate identical or corresponding features throughout the several views. The drawings show a number of preferred features of the present inventive fitness platform.

FIG. 1 is a block diagram diagrammatically showing an exemplary personalized data collection system 100 comprising remote personal input sources for a user 1 of the present invention in one preferred embodiment. In this embodiment, data input system 100 includes genetic testing module 10, remote personalized data input computer 12, the ALTER two-way exercise exerciser-tracking, visual monitoring screen or mirror 14, data input mobile device 16, data collecting wrist strap 18, which may be used for both sleep tracking and all-day monitoring of various metrics obtainable from such a strap, and heart monitor 20. Each of these devices, are designed to transmit via a network or networks personalized user data collected from individual users of the platform of the present invention to centralized database 50, for processing both offline and in real time in the fitness and health recommendation engine of the present invention to be discussed hereinafter.

Figure 2:
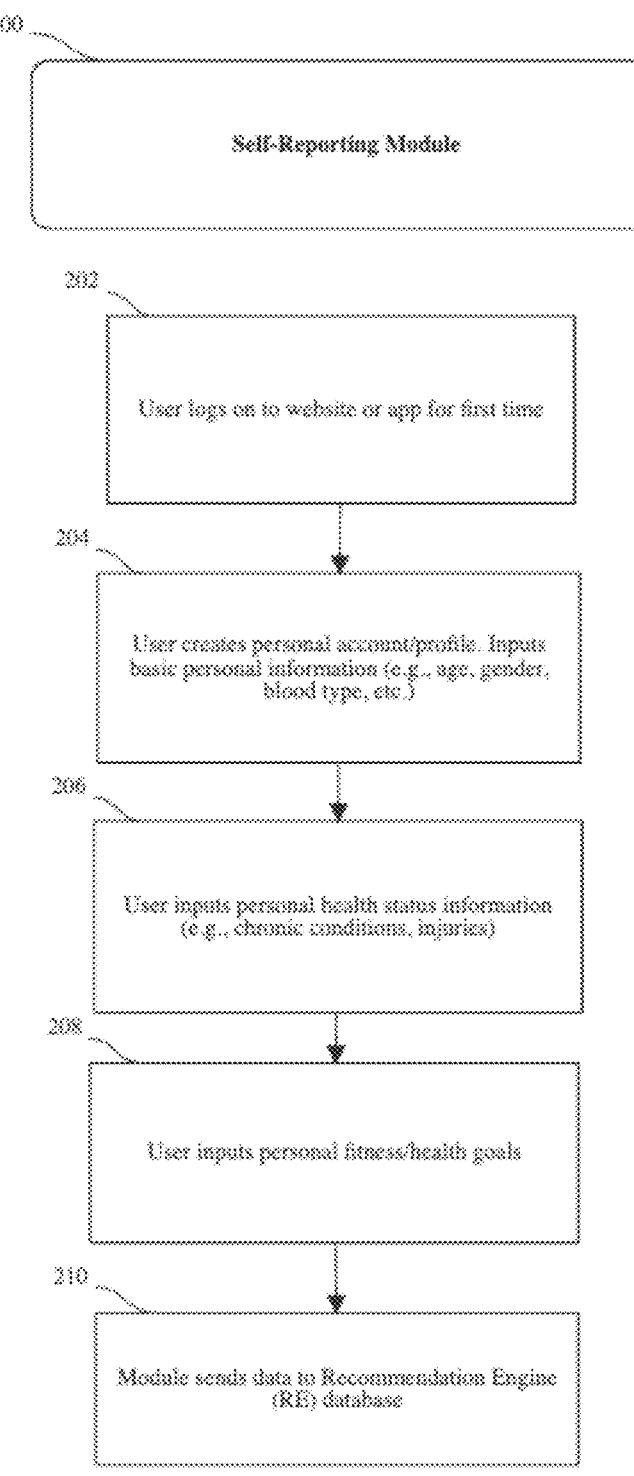
FIG. 2 is a simplified flow diagram showing the operation of a self-reporting input module according to one embodiment of the present invention

FIGS. 2-6 are diagrams showing one preferred flow of customer user information to be collected by the various external devices and systems shown in FIG. 1. Referring to FIG. 2, self reporting module 200 in one embodiment is disclosed. In step 202, user logs onto the ALTER website on computer 12 or mobile device 16 and in step 204 creates a user account, inputting basic personal information. The data collected may be age, gender, blood type, personal goals, and a host of other inputs. In step 206, the user enters personal health status, such as conditions, injuries, or other factors relevant to fitness planning. In step 208, user is optionally presented with a screen to input her personal fitness goals and personal health goals. In step 210, computing device 12 or 14 sends the collected information to a Recommendation Engine (RE) database 50 as further discussed.

Figure 3:
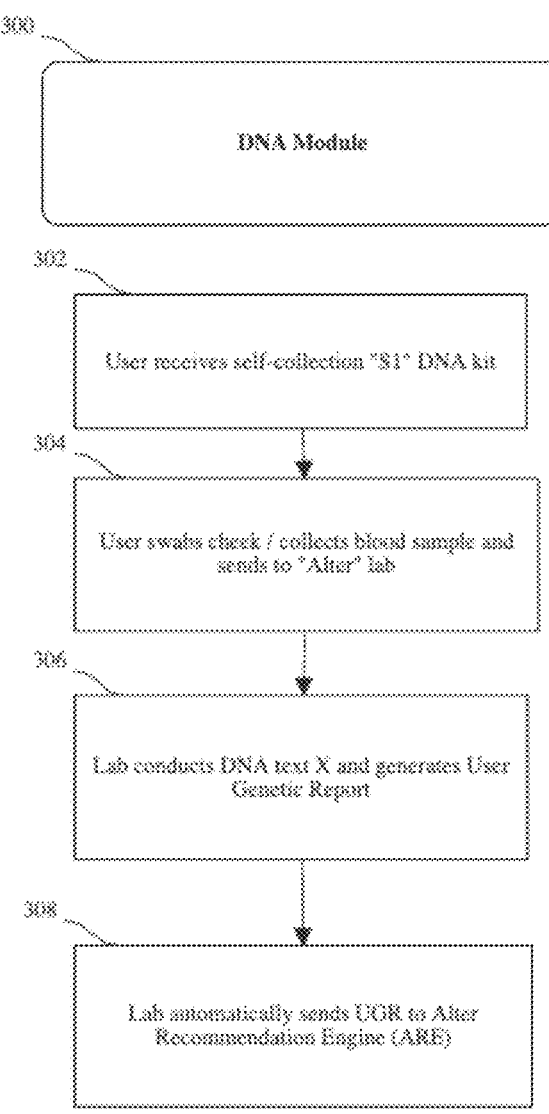
FIG. 3 is a simplified flow diagram showing the operation of a personalized DNA input module according to one embodiment of the present invention.

FIG. 3 describes the operation of DNA module 300 in one preferred embodiment of the present invention. In step 302, the operator of the system mails or otherwise sends a self-collection DNA kit to, and is received by, user 1. In step 304, user 1 collects a DNA sample. In preferred embodiments, the collection kit comprises a cheek swab for placement in a sanitary container to be sealed and mailed to a DNA test lab. Alternatively, the collection may be a blood sample. In step 306, the lab conducts DNA testing on user 1's sample. This is specific for metrics relevant to a person's health, strength and may also reveal potential genetic disorders, as will be understood by those skilled in the art. The lab then generates personalized genetic report. Finally, in step 308, the lab sends the report to the ALTER Recommendation Engine database 50.

Figure 4:
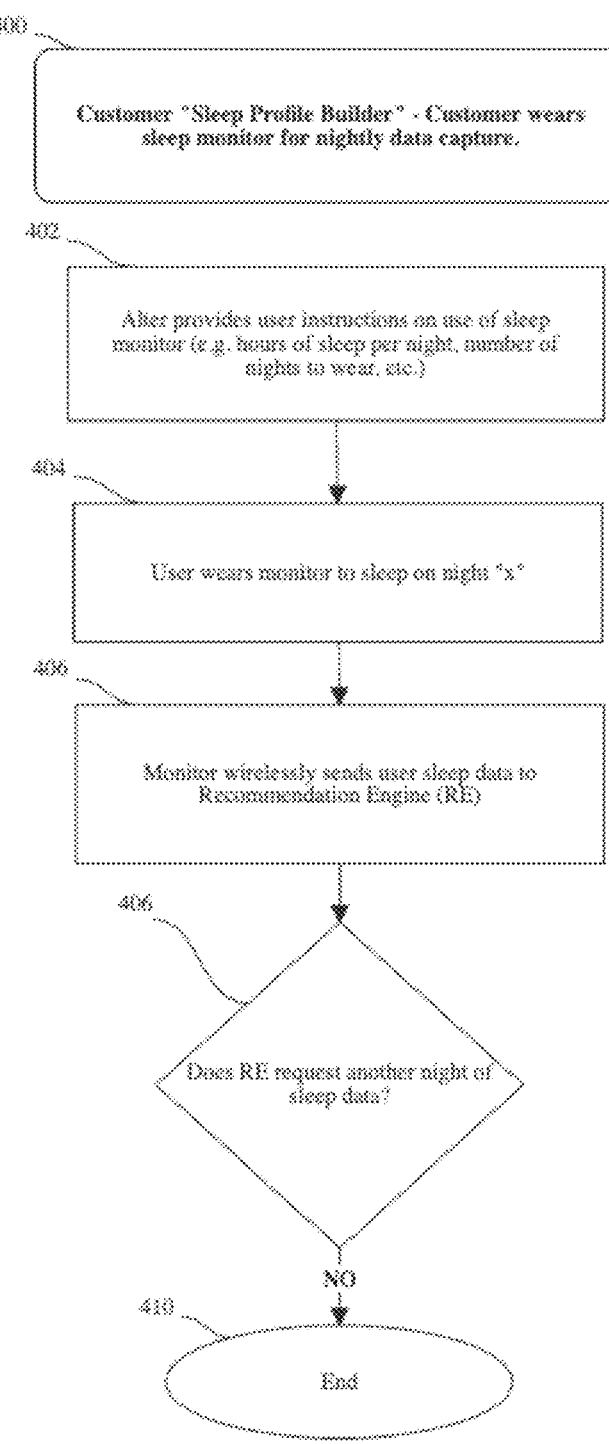
FIG. 4 is a simplified flow diagram showing the operation of a sleep profile builder input module according to one embodiment of the present invention.

FIG. 4 discloses the data flow for a Customer Sleep Profile module 400, which is worn by user 1. In step 402, the system, having sent to user 1 a sleep tracker or monitor such as a sleep wrist strap 18, provides user 1 with instructions on how to use tracker 18, including the number of hours to use it, the number of nights to use it, etc. It should be understood that to the extent the term sleep monitor implies a device that meets certain regulatory or standards requirements to be called a "monitor", either a monitor or a sleep tracker may be used, and all types are within the scope of the present invention. In step 404, user 1 wears tracker/monitor 18 to sleep on night x, where x=1. The monitor 18 in step 406 monitors the sleep patterns of user overnight and automatically, wirelessly send the data to Recommendation Engine database 50. Optionally, the RE may assess the data for quality and quantity and be programmed to determine whether in step 408 another night of sleep data is requested. If the answer is yes, then x=2 and user wears the monitor another night which sends night 2 data to the RE database 50. This process is repeated until RE does not request additional nights of data and steps collecting in step 410.

Alternatively, the user instructions may instruct user to wear sleep monitor for a set number of days without the feedback loop. Moreover, in preferred embodiments, monitor or tracker 18 is not limited to capturing user data during sleep period. Rather, device 18 is also designed to measure all day activity and daily readiness, as will be discussed further below.

Figure 5:
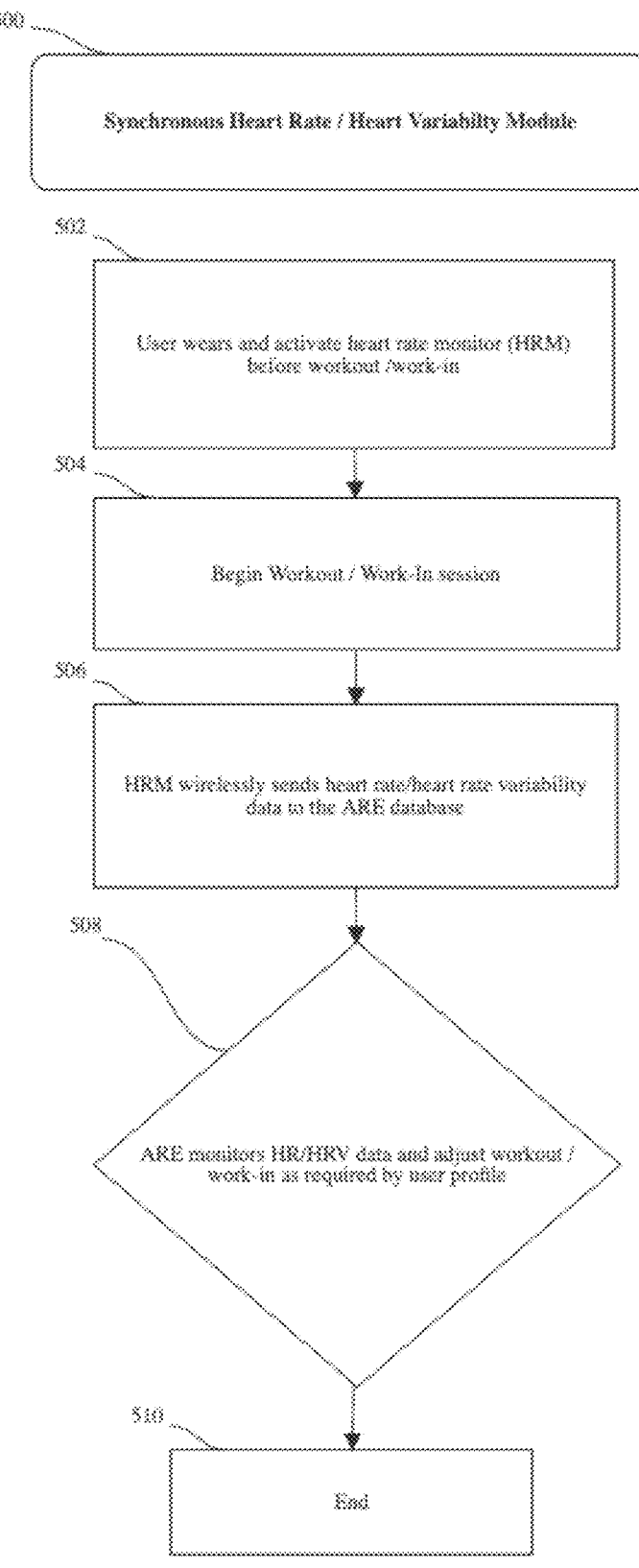
FIG. 5 is a simplified flow diagram showing the operation of a synchronous heart performance input module according to one embodiment of the present invention.

One embodiment of a synchronous Heart Rate Module 500 is now described in FIG. 5. In step 502 user received and wears a heart monitor 20. In step 504, user begins a workout or work-in session. Monitor 20 may monitors heart function, such as heart rate and hear rate variability, and in step 506 wirelessly sends the data to RE database 50. RE ingests heart data in 508 and decides whether to collect additional heart data. If yes, the flow loops back to step 506. If not, the process ends in step 510. It should be appreciated that device 18 and device 20 need not be separate devices, but the functionality of both may reside in one device that placed on a user's wrist or other location on the body.

As another preferred input to the RE, in preferred embodiments the ALTER two-way, visual monitoring screen 14 works in concert with various software modules to capture additional user metrics, asynchronously. That is, when a user first logs onto the ALTER system and stands "before the ALTER", the visual system incorporated in device 14 may capture 2-dimensional body images of the user to create a 2-D initial body composition assessment. In other embodiments, the imaging system may be capable of capturing more sophisticated 3-D body images to create a 3-D body composition assessment. In some implementations, the system may be scheduled to take periodic body images captured at planned intervals (every few weeks or months), and will be able to compare the body compositions from period to period or overall body composition progress toward a user goal.

In one preferred embodiment, the recommendation system 10 of the present invention also implements a synchronous vision module 600 as shown in FIG. 6. In step 602, user begins a workout or work-in session in front of the ALTER mirror 14 that includes a digital vision module that tracks the exerciser's positions (e.g., posture) and movements. Thus, in step 604, with an exercise routine in progress-via in preferred embodiments, a virtual or live trainer projected through mirror 14—the vision system monitors exerciser/user 1, and in step 606 compares her movements to a database of "referenced movement standards" that are comprise "proper" form and movements. In step 608, RE engine asks if the movements are "correct" or "incorrect". If incorrect, mirror 14 will visually instruct exerciser how to correct the positioning of the body or movement during the exercise. This is done continuously until the exercise set is complete in step 610.

Figure 7:
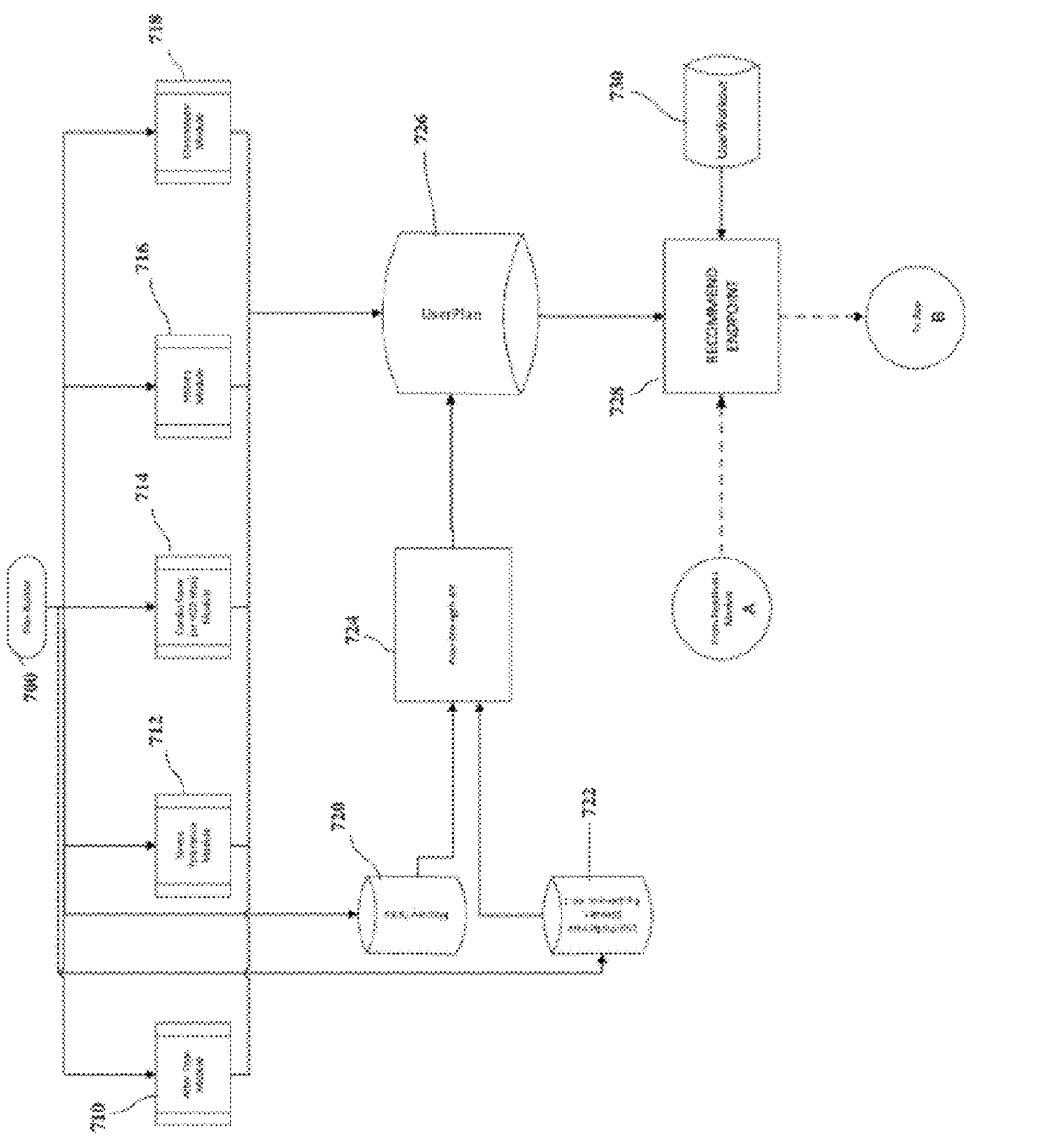
FIG. 7 is a high-level block diagram showing the modules of a personalized exercise plan builder/recommendation engine for one embodiment of the ALTER fitness platform of the present invention.

FIG. 7 shows one functional block diagram and data flow for one embodiment of a data collection and recommendation engine invention according to the present invention called "Plan Builder" 700. The goal here is to conclude with a Recommendation Endpoint 728 from which system 1000 of the present invention can make personalized fitness and wellness recommendations. As seen, Recommendation Endpoint 728 takes inputs from (i) UserPlan 726, (ii) Readiness module 800 (See FIG. 8) and (iii) User Workout data 730.

In this embodiment, UserPlan 726 gets its inputs from (a) the outputs of five (5) input modules in the system, namely "Alter Type" module 710, stress tolerance module 712, VO2 Max module 714, History Module 716 and Chronotype module 718; and (b) UserPreference database 722 and MasteryTable 720 via a PEAR Strength API 724. It should be understood that these input modules are exemplary and optional. More, fewer or different input modules may be used in practice. For example, the VO2 Max module may be a VO2 (not Max) module, or it may simply be a "Cardio Fitness Level" module that ascertains fitness level via extrapolation from heart rate data and workload.

Figure 8:
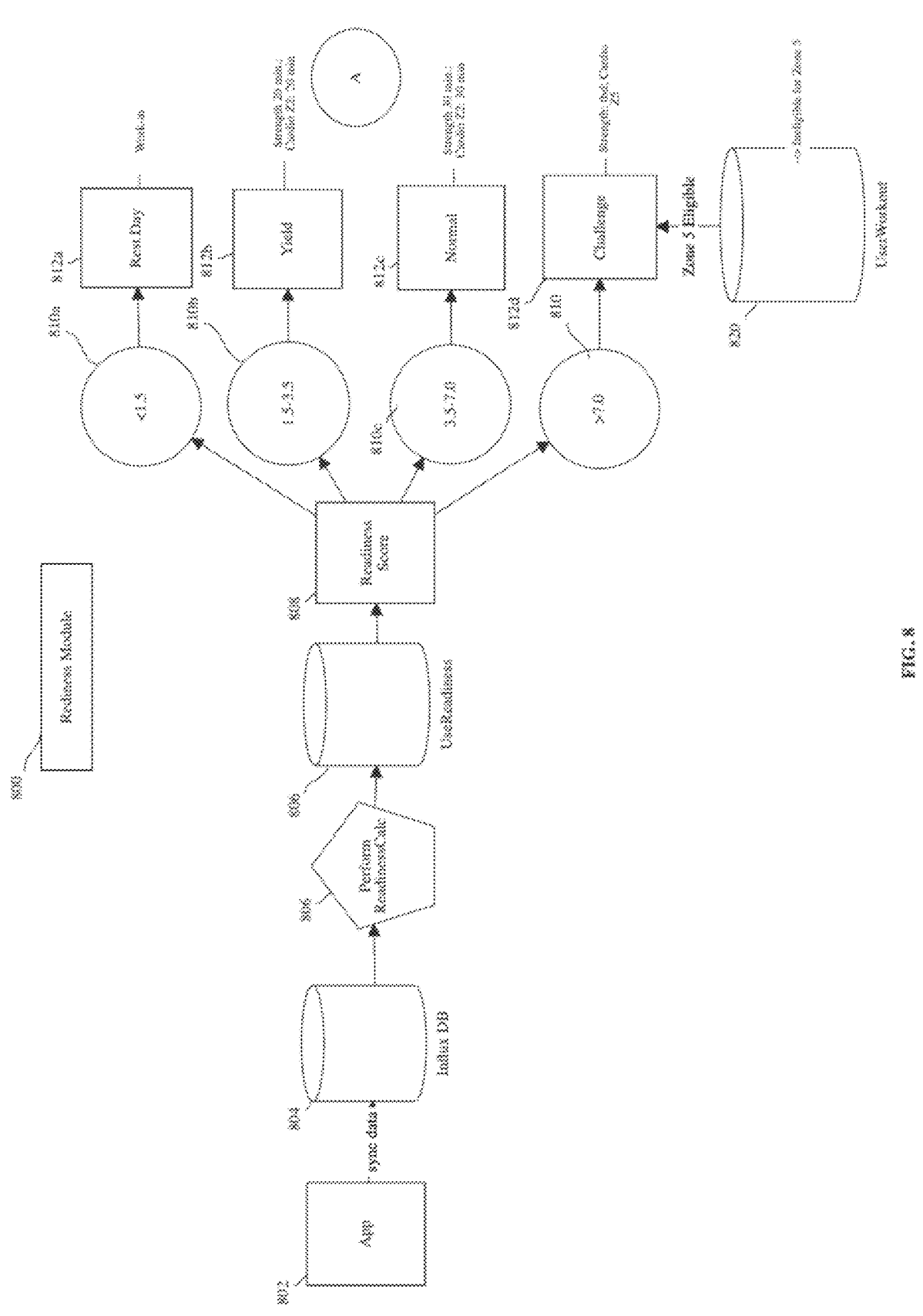
FIG. 8 is a high-level block diagram showing one implementation of a user readiness module of the present invention used as an input to the recommendation engine shown in FIG. 7.

As seen in FIG. 8, Readiness module 800, creates a UserReadiness score indicating how "Ready" user is for an intense cardio or strength exercise session or not. This is done by having user 1 perform a preliminary readiness call via an app. As seen, this score is input to UserWorkout database 730 which in turn makes a recommendation: a low readiness score leads to a recommended lower cardio zone (among, in this embodiment, 5 zones) and less vigorous User Workout or even a rest day (for a score of <1.5), and a higher readiness scores lead to more challenging and longer workout recommendations. Again, this data is input into the recommendation endpoint 728. It should be understood that the scores and correlated recommendations in these figures are exemplary and are not set or required. Thus, for example, looking at Readiness module 800, a score >7 does not always trigger a "challenge" or zone 5 (Z5) workout even if user 1 is eligible. The challenge workouts may be triggered on a 80:20 ratio or 4 smart zone to 1 challenge zone ratio.

Figure 9:
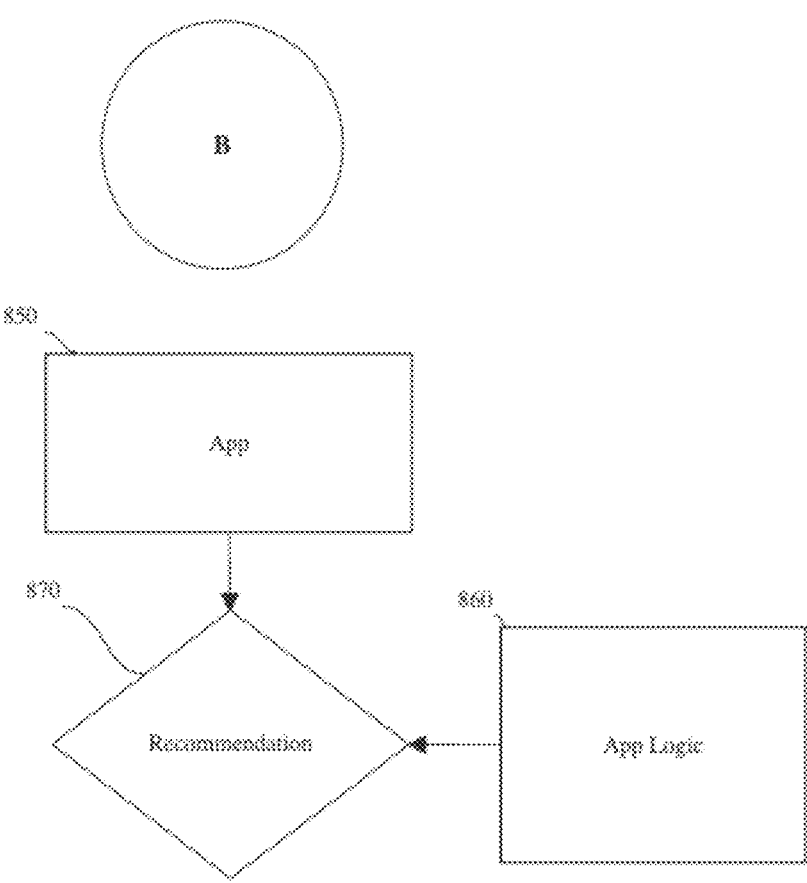
FIG. 9 is a block diagram for an app that may be used with the present invention.

Moving along the flow of this process, as seen in FIG. 7 and FIG. 9, all this data collected at endpoint 728 is sent to an application 850, which together with app logic 860 combine to result in a workout or work-in recommendation 870 for user 1.

Figure 10:
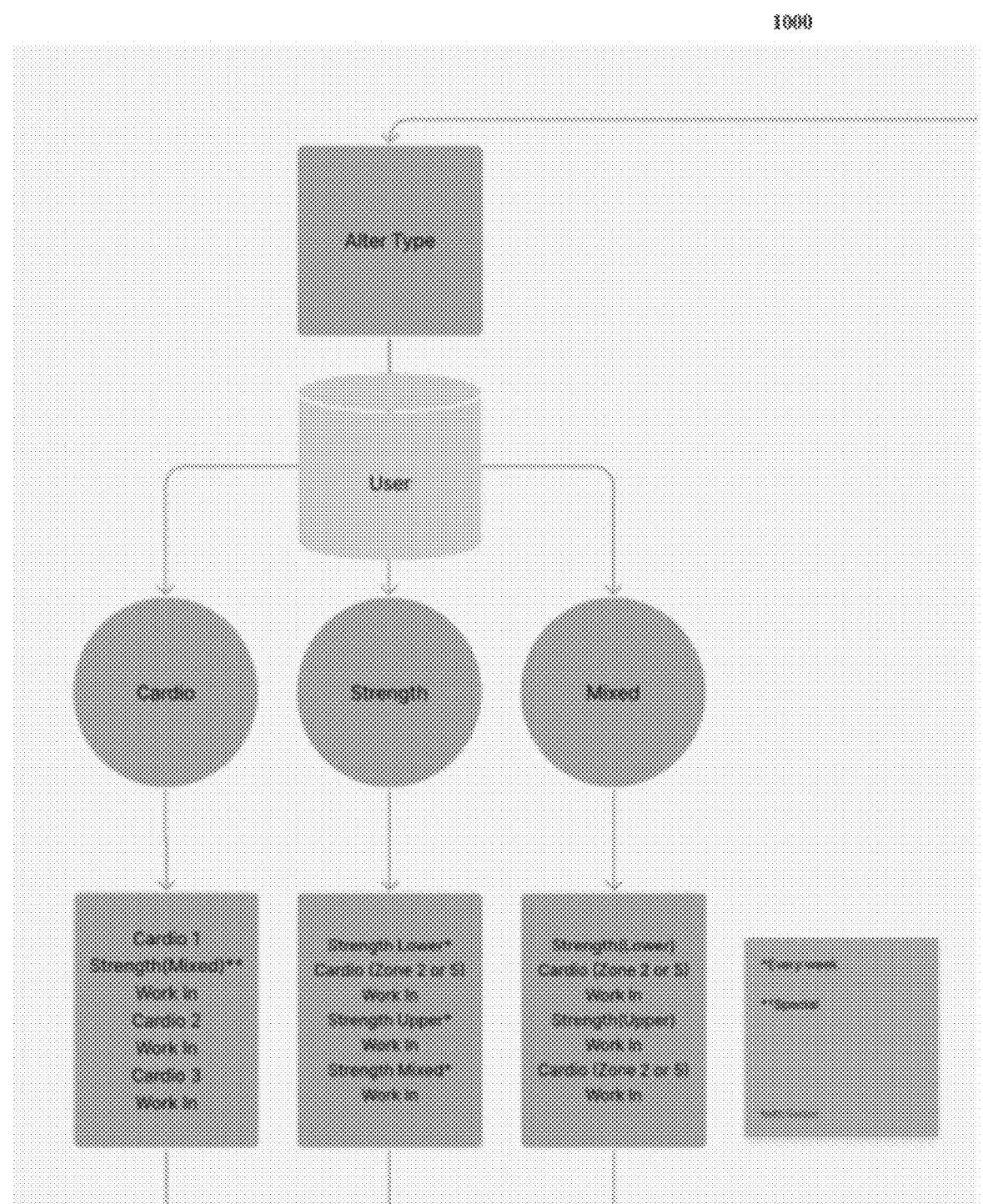
FIGS. 10-14 are partial block diagrams showing the flow of external input modules into the system of one embodiment of the present invention.
Figure 11:
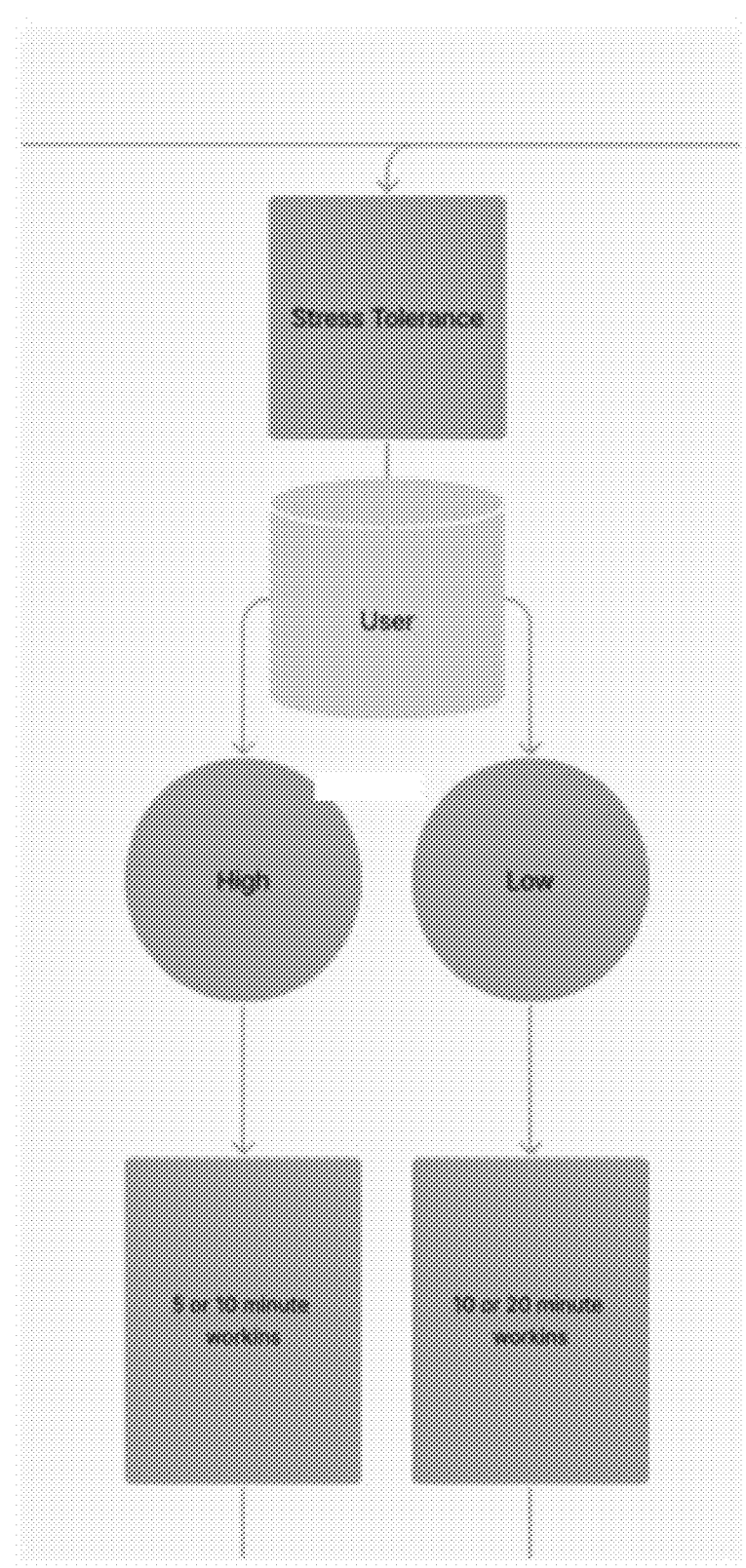
Figure 12:
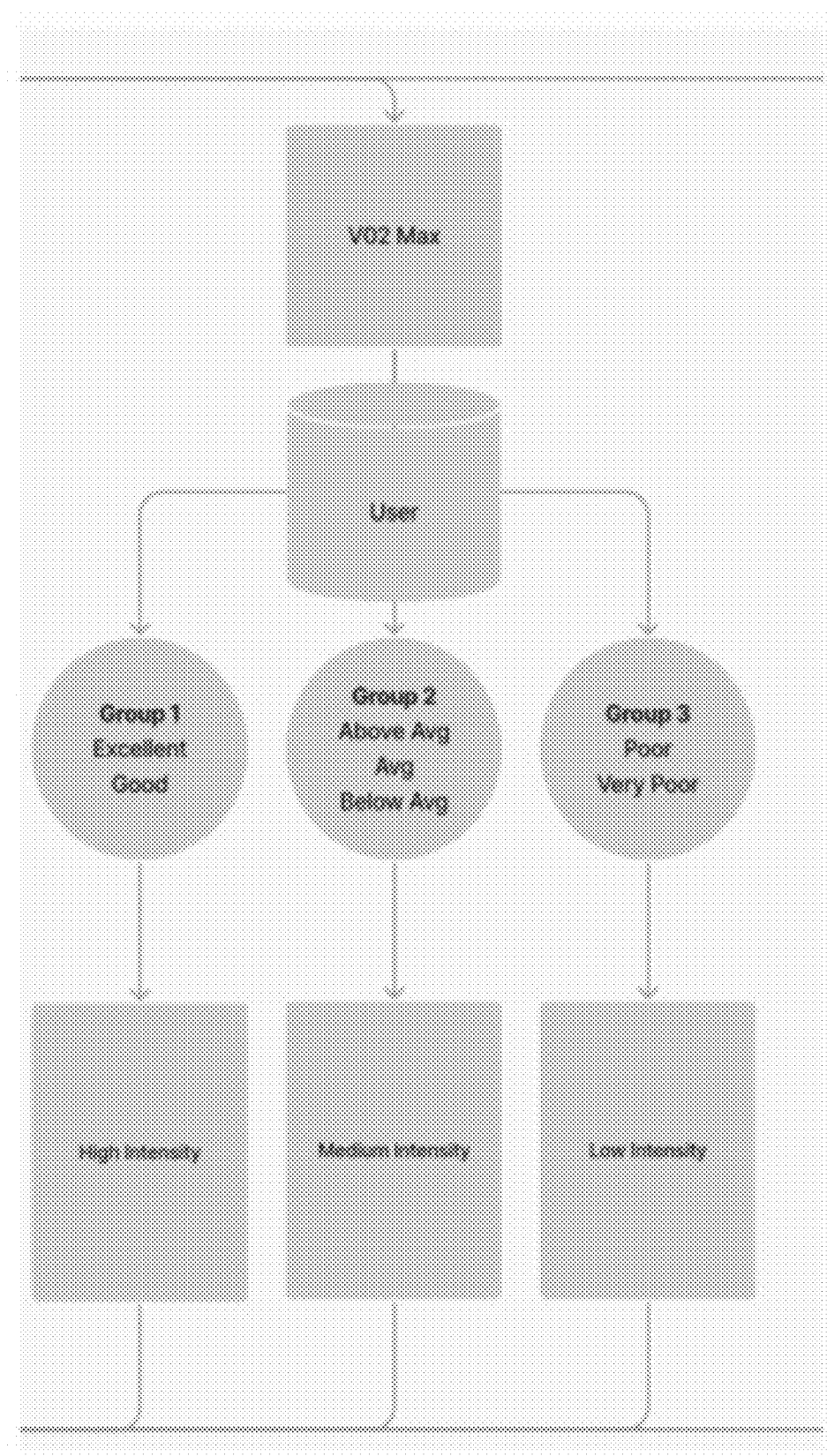
Figure 13:
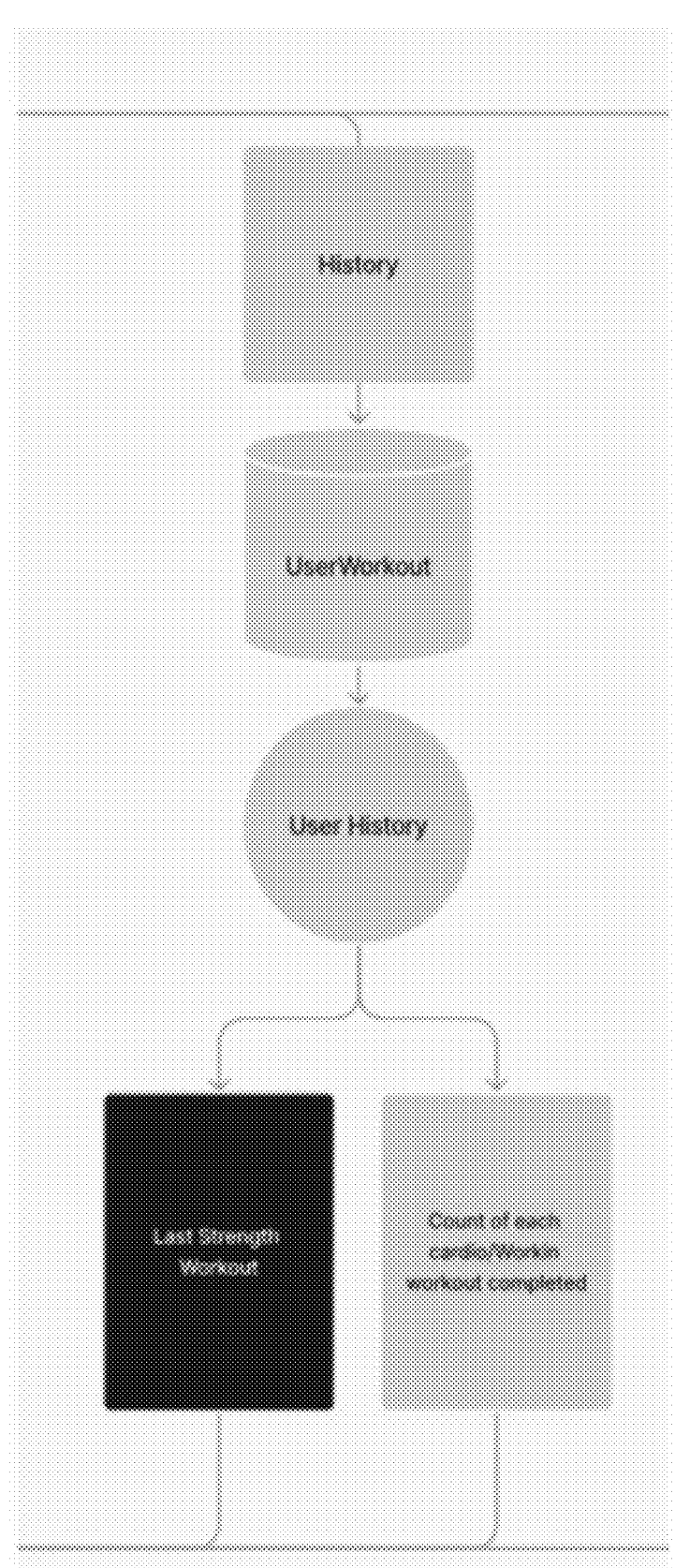
Figure 14:
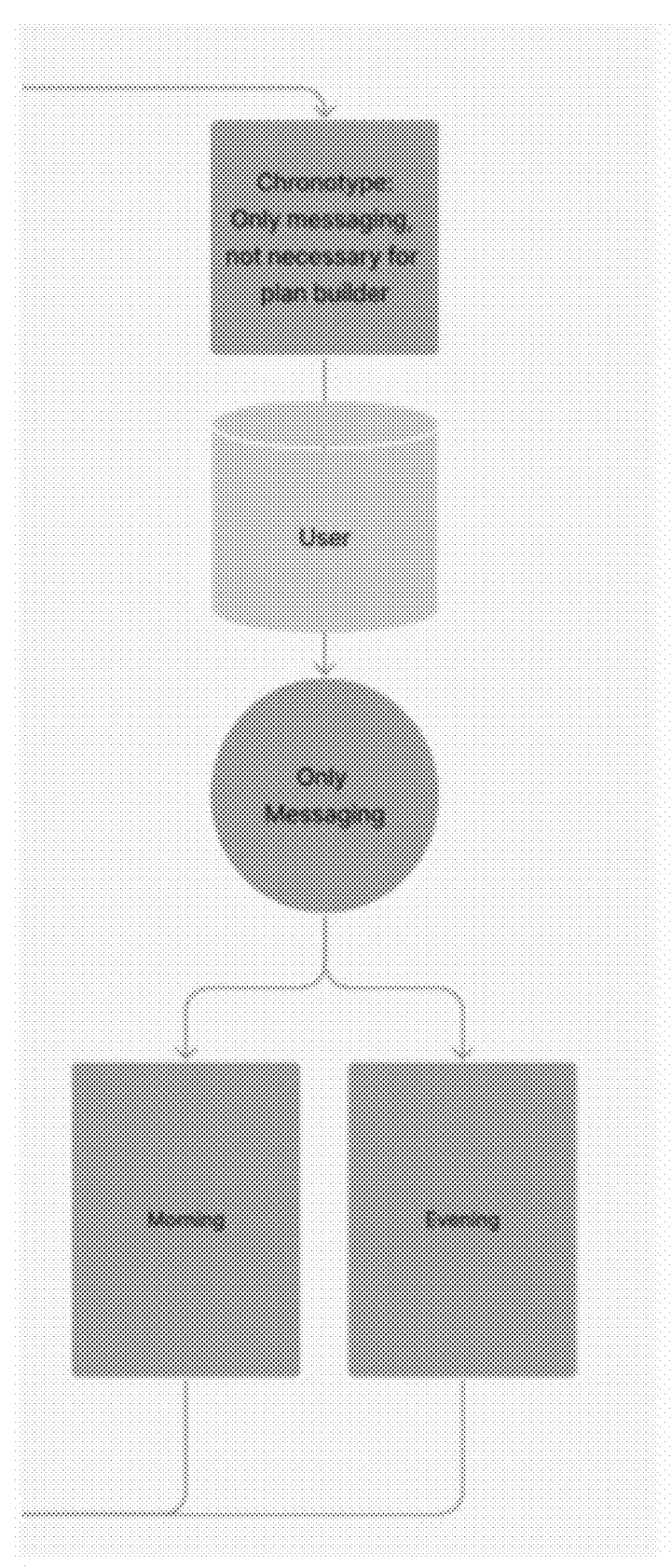

FIGS. 10-14 show details of the five (5) external input modules in the system of one embodiment of the invention, namely "Alter Type" module 710 (FIG. 10), Stress tolerance module 712 (FIG. 11), VO2 Max module 714 (FIG. 12), Personal History Module 716 (FIG. 13) and Chronotype module 718 (FIG. 14). As seen in FIG. 10, "Alter Type" module 710 is designed to have the system define/recommend for User 1 a cardio, a strength, or a mixed workout/work-in plan, including the days in a week which will involve various intensity workouts, with other days being work-in days. As seen in FIG. 12, VO2 Max (or Cardio Readiness) module will take output from the heart monitor for User 1 and looking at her V02 or Cardio scores place her in a Group 1, 2 or 3, from excellent cardio fitness to poor fitness. This in turn will result in the Alter recommendation engine (ARE) planning high intensity, medium intensity, or low intensity workout. It is understood that because the system constantly monitors the VO2 (or more broadly the Cardio fitness) of User as long as she wears the heart monitor, the User can move from one group to the next as her fitness improves (or degrades).

History module shown in FIG. 13, monitors the history of UserWorkouts, both strength and cardio/work-ins recently completed, and uses it to recommend a plan for the present. FIG. 14 shows the use of User Chronotype; that is, whether the user is a morning or evening exerciser. This is currently only used for messaging, but in present and future implementation may also be used plan building.

All of the data inputs that are input into the ARE may also be integrated, not just for a customized user life plan, but also to create a snapshot, the inventors call an ALTER INDEX or ALTER SCORE of the user's state, indicative of the user's overall health and fitness. This or these outputs may be an aggregate of some or all of the personalize inputs discussed and others, including a cardio score, strength score, "zen score", body composition score, sleep scope and so on.

Finally, it should be understood that recommendation system of the present invention may be implemented in hardware and software as shown in FIG. 5. Thus, in embodiments, recommendation engine includes memory 3010 with memory program 3014 and data 3020, CPU 3005, storage medium 3030, I/O Interface 3035, and user interface 3040 and potentially multimedia interface 3045.

The automated personalized exercise recommendation engine has several advantages over traditional exercise recommendations. By incorporating DNA input, sleep metrics, and visual sensing, the engine can provide more tailored and precise exercise recommendations, leading to better outcomes and improved overall health and fitness.

The camera-equipped screen or mirror of the present invention that preferably plays exercise videos through screen 14, is an important part of the system, opening up many options for design and user alike. Thus, the system with mirror can build and deliver a customized/personalized, snip-based, video workouts or work-ins to user based on the RE outputs for that user. Following are some features of the screen:

In embodiments, screen 14 may be a mirror type screen, customized, that is personalized to the measured attributes and observed and expressed preferences of the user for example. The screen and preferably built-in (but can be external) camera system may tack movement mastery level of the user against movement categories, where mastery is calculated based on any one or more of the following: (a) user progression through a mastery framework; (b) a user's ability to perform the movement; or recorded history of having performed the movement OR (c) some combination of the two.

The system may build and the screen may play a collection of exercises, categorized within movement categories based on visual recognition feedback, or recorded user performance based on other Alter system sensors aggregation, and scoring based on the feedback from Heart Rate sensors and other parts of Alter's wearable sensor ecosystem, including heart rate and other heart-based measurements and inferences HRV (IBI), respiratory rate, activity, sleep, sleep mode etc.

The exercise system may provide "snip-based" looping video of individual movements. This can be presented to user with or without introductory video and audio content setting up the exercise. This may include demonstrations, evaluation sequences, and corrections of particular exercises.

Moreover, the system A/V recommendations may be delivered to different devices. Presentation may be visual on screen, visual on phone, audio speakers on screen, visual headphones. Moreover, the content may be cast to a different screen for a multi-screen experience.

The Audio/Video Content-Workouts may be presented as video and audio content. They may be guided, demonstrated exercises or either. In some embodiments, the content will be longform video. In others composite clip based and looping video of movements. Or it may be composite clips based with/pauses for rest time. It is understood that pause times can be customized and personalized based on measured cardio, respiratory and/or movement performance.

Work-in video and audio content may include animations & looping video. Specific colors may used within videos based on light color theory.

Gamification Option—The workouts and work-ins can be gamified to incentive users to user the system. These games presented on the mirror display or mobile device or otherwise, may relate to advancing through the mastery levels within any movement category. It may include scoring and tracking over time how users perform during and as a result of "work" through long term measures relating to, for example: mobility; strength; or movement mastery (within movement categories and modalities) and performance consistency over time.

Right Fit Option—The present invention is well-adapted for providing a way of evaluating the "right fit" of a hand weight to personalize a strength workout for an individual. For example, in use in a strength workout, a person may be exercising using a hand weight or kettlebell of known or unknown weight, the screen can be programmed to sense using a "form recognition" system and provide feedback about reps, timing, and form timestamps. Thus, the system may improve the form of weightlifters by recommending proper motion with weight (a particular recommended exercise) performed in front of the camera.

Machine learning and AI language models may be implemented in the present invention so that the system self-learns its users' needs, corrections, and growth plans and adjusts them on the fly. As the system database of users grows, the system will be able to refine it recommendations to each individual user. This can create a brand new platform and database for use by 3rd parties as they develop new exercise and fitness tools.

While embodiments of the invention have been illustrated and described, it is not intended that these embodiments illustrate and describe all possible forms of the invention. Various changes, modifications, and alterations in the teachings of the present invention may be contemplated by those skilled in the art without departing from the intended spirit and scope thereof. It is intended that the present invention encompass such changes and modifications.

The invention claimed is:

1. A multi-source input fitness and health recommendation system for a user, comprising:
   (a) one or more processors; and
   (b) one or more non-transitory computer-readable storage media storing instructions that, when executed by the one or more processors, cause the one or more processors to
      i. receive user fitness data from a plurality of heterogeneous input sources, the heterogeneous input sources including at least one asynchronous input source relating to one health state or condition of the user and at least one synchronous input source relating to another health state or condition of the user;
      ii. aggregate the received user fitness data into a unified user fitness profile stored in a recommendation engine database;
      iii. generate one or more user readiness scores and fitness classifications by applying predefined scoring logic to the unified user fitness profile;
      iv. generate a personalized exercise plan for the user, the personalized exercise plan comprising workout and optionally work-in parameters, the workout and optional work-in parameters selected based at least in part on the one or more readiness scores and fitness classifications; and
      v. output one or more exercise recommendations to the user via a user interface, including providing real-time feedback during a fitness event based on additional synchronous user fitness data.

2. The system of claim 1, wherein the at least one asynchronous input source includes one or more of a self-reporting reports, a captured DNA report, and a sleep tracker.

3. The system of claim 1, wherein the at least one synchronous input source includes one or more of a visual sensor for capturing user movement, heart rate monitor, heart rate variability monitor, and a self-reporting report during a fitness event.

4. The system of claim 1, wherein the workout parameters include an exercise type, a number of reps per exercise type, a number of sets per exercise type, and rest periods between the number of sets.

5. The system of claim 1, wherein the executed instructions further cause the one or more processors to create and export a customized exercise and fitness report for the user.

6. A non-transitory computer-readable storage medium storing computer-readable instructions that, when executed by one or more processors of a fitness and health recommendation system, cause the one or more processors to, i. receive user fitness data from a plurality of heterogeneous input sources, the heterogeneous input sources including at least one asynchronous input source relating to one health state or condition of the user and at least one synchronous input source relating to another health state or condition of the user;

ii. aggregate the received user fitness data into a unified user fitness profile stored in a recommendation engine database;

iii. generate one or more user readiness scores and fitness classifications by applying predefined scoring logic to the unified user fitness profile;

iv generate a personalized exercise plan for the user, the personalized exercise plan comprising workout and optionally work-in parameters, the workout and optional work-in parameters selected based at least in part on the one or more readiness scores and fitness classifications; and v. output one or more exercise recommendations to the user via a user interface, including providing real-time feedback during a fitness event based on additional synchronous user fitness data.

\* \* \* \* \*